United States Patent
Wei et al.

(10) Patent No.: US 12,140,596 B2
(45) Date of Patent: *Nov. 12, 2024

(54) KITS, MICROFLUIDICS DEVICES, AND METHODS FOR PERFORMING BIOTIN ASSAYS

(71) Applicant: Siemens Healthcare Diagnostics Inc., Tarrytown, NY (US)

(72) Inventors: Tie Q Wei, Wilmington, DE (US); Zhu Teng, Garnet Valley, PA (US); Xiaodong Liu, Wilmington, DE (US); Martin Drinan, Newark, DE (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 846 days.

This patent is subject to a terminal disclaimer.

(21) Appl. No.: 17/250,173

(22) PCT Filed: Jul. 24, 2019

(86) PCT No.: PCT/US2019/043195
§ 371 (c)(1),
(2) Date: Dec. 8, 2020

(87) PCT Pub. No.: WO2020/028110
PCT Pub. Date: Feb. 6, 2020

(65) Prior Publication Data
US 2021/0247398 A1 Aug. 12, 2021

Related U.S. Application Data

(60) Provisional application No. 62/711,694, filed on Jul. 30, 2018.

(51) Int. Cl.
*G01N 33/58* (2006.01)
*B01L 3/00* (2006.01)
*G01N 21/76* (2006.01)

(52) U.S. Cl.
CPC ...... *G01N 33/582* (2013.01); *B01L 3/502715* (2013.01); *G01N 21/76* (2013.01); *B01L 2200/027* (2013.01); *B01L 2200/16* (2013.01)

(58) Field of Classification Search
CPC ...... G01N 33/582; G01N 21/76; G01N 33/58; G01N 33/583; B01L 3/502715;
(Continued)

(56) References Cited

U.S. PATENT DOCUMENTS

| 5,340,716 A | 8/1994 | Ullman et al. |
| 11,287,429 B2 * | 3/2022 | Wei ............ B01L 3/502715 |

(Continued)

FOREIGN PATENT DOCUMENTS

| CN | 102892896 | 1/2013 |
| JP | 2017508971 | 3/2017 |

(Continued)

OTHER PUBLICATIONS

Yasgar et al. AlphaScreen-Based Assays: Ultra-High-Throughput Screening for Small-Molecule Inhibitors of Challenging Enzymes and Protein-Protein Interactions. Methods Mol Biol. 2016 ; 1439: 77-98. (Year: 2016).*

(Continued)

*Primary Examiner* — Shafiqul Haq

(57) ABSTRACT

Kits containing a chemiluminescent detection system and microfluidics devices and methods for determining the concentration of biotin in a sample are disclosed. The kits, microfluidics devices, and methods utilize a sensitizer capable of generating singlet oxygen in its excited state and having avidin or an analog thereof directly or indirectly bound thereto, as well as a singlet oxygen-activatable chemiluminescent compound having biotin or an analog thereof directly or indirectly bound thereto.

13 Claims, 6 Drawing Sheets

(58) Field of Classification Search
CPC ........... B01L 2200/027; B01L 2200/16; C09K 11/07; F21K 2/06
See application file for complete search history.

(56) References Cited

U.S. PATENT DOCUMENTS

| | | |
|---|---|---|
| 2005/0208598 A1 | 9/2005 | Cox et al. |
| 2012/0077284 A1 | 3/2012 | Soldo et al. |
| 2013/0084652 A1 | 4/2013 | Shapir et al. |
| 2013/0310570 A1 | 11/2013 | Boons et al. |
| 2014/0154700 A1 | 6/2014 | Teng et al. |
| 2016/0033417 A1* | 2/2016 | Ledden .................... F21K 2/06 422/52 |
| 2018/0003700 A1* | 1/2018 | Fogelstrand ....... G01N 33/5306 |
| 2021/0247399 A1* | 8/2021 | Wei ........................ G01N 21/76 |

FOREIGN PATENT DOCUMENTS

| | | |
|---|---|---|
| WO | 2005080989 | 9/2005 |
| WO | 2016164488 | 10/2016 |

OTHER PUBLICATIONS

Ullman E. F. et al; "Luminescent oxygen channeling assay (LOCI): sensitive, broadly applicable homogeneous Immunoassay method"; Clinical Chemistry, American Association for Clinical Chemistry, Washington, DC; vol. 42; No. 9; pp. 1518-1526; Jan. 1, 1996.

Claire E Chivers et al: "A streptavidin variant with slower biotin dissociation and increased rnechanostability", Nature Methods, Nature Pub. Group, New York, vol. 7, No. 5, May 1, 2010, pp. 391-393.

International Search Report for PCT/US2019/043195 dated Oct. 7, 2019.

* cited by examiner

KITS, MICROFLUIDICS DEVICES, AND METHODS FOR PERFORMING BIOTIN ASSAYS

CROSS REFERENCE TO RELATED APPLICATIONS/INCORPORATION BY REFERENCE STATEMENT

The subject application claims benefit under 35 USC § 119(e) of U.S. provisional Application No. 62/711,694, filed Jul. 30, 2018. The entire contents of the above-referenced patent application are hereby expressly incorporated herein by reference.

STATEMENT REGARDING FEDERALLY SPONSORED RESEARCH OR DEVELOPMENT

Not Applicable.

BACKGROUND

Biotin is often used in a conjugate with antibodies or other small drug molecules for assay reagents. The tight binding of biotin to large protein molecules (e.g., avidin and streptavidin) that are coated on a solid support provides a convenient way to immobilize the antibodies or drugs on the solid support.

Biotin is well known in the art for its use as a food supplement; for example, biotin is utilized to promote healthy hair and nail growth and to treat various disease conditions. Given this use, significant biotin levels can be found in biological samples, such as (but not limited to) blood. Since biotin is used in many diagnostic assays (for example, to coat solid supports), high levels of biotin in test samples can interfere with assay signals in any assays where biotinylated assay components are employed. Because interference is observed in various assay methods at different biotin concentrations, the levels of biotin present in patient samples should be quantitated to determine if the samples are suitable for use in particular assays. However, most currently available biotin assays have narrow ranges (i.e., 0-50 ng/ml) that are not suitable for detecting the wide dynamic range of biotin concentrations that are typically found in actual patient samples (i.e., 0-1500 ng/ml).

The only method for handling the narrow detection range for currently available biotin assays is to perform serial dilutions of the test sample to hopefully attain the expected assay range; however, this is a cumbersome process that wastes test sample as well as reagents and also slows down the turnaround time.

The field of medical diagnostics utilizes many different forms of assay technologies. One example of a commercially used assay is the Luminescent Oxygen Channeling Assay (LOCI®) technology. The LOCI® advanced chemiluminescence assay is described, for example, in U.S. Pat. No. 5,340,716 (Ullman et al.), the entire contents of which are expressly incorporated herein by reference. The currently available LOCI® technology has high sensitivity and uses several reagents. In particular, the LOCI® assay requires that two of these reagents (referred to as a "sensibead" and a "chemibead") be held by other specific binding partner assay reagents in a manner whereby the sensibead and chemibead are in close proximity to one another to achieve a signal. Upon exposure to light at a certain wavelength, the sensibead releases singlet oxygen, and if the two beads are in close proximity, the singlet oxygen is transferred to the chemibead; this causes a chemical reaction that results in the chemibead giving off light that can be measured at a different wavelength.

However, there are no biotin assays available in the LOCI® format.

Therefore, there is a need in the art for new and improved assays for biotin that overcome the disadvantages and defects of the prior art. It is to such assays, as well as kits and microfluidics devices containing same and methods of using same, that the present disclosure is directed.

DETAILED DESCRIPTION

Figure 1:
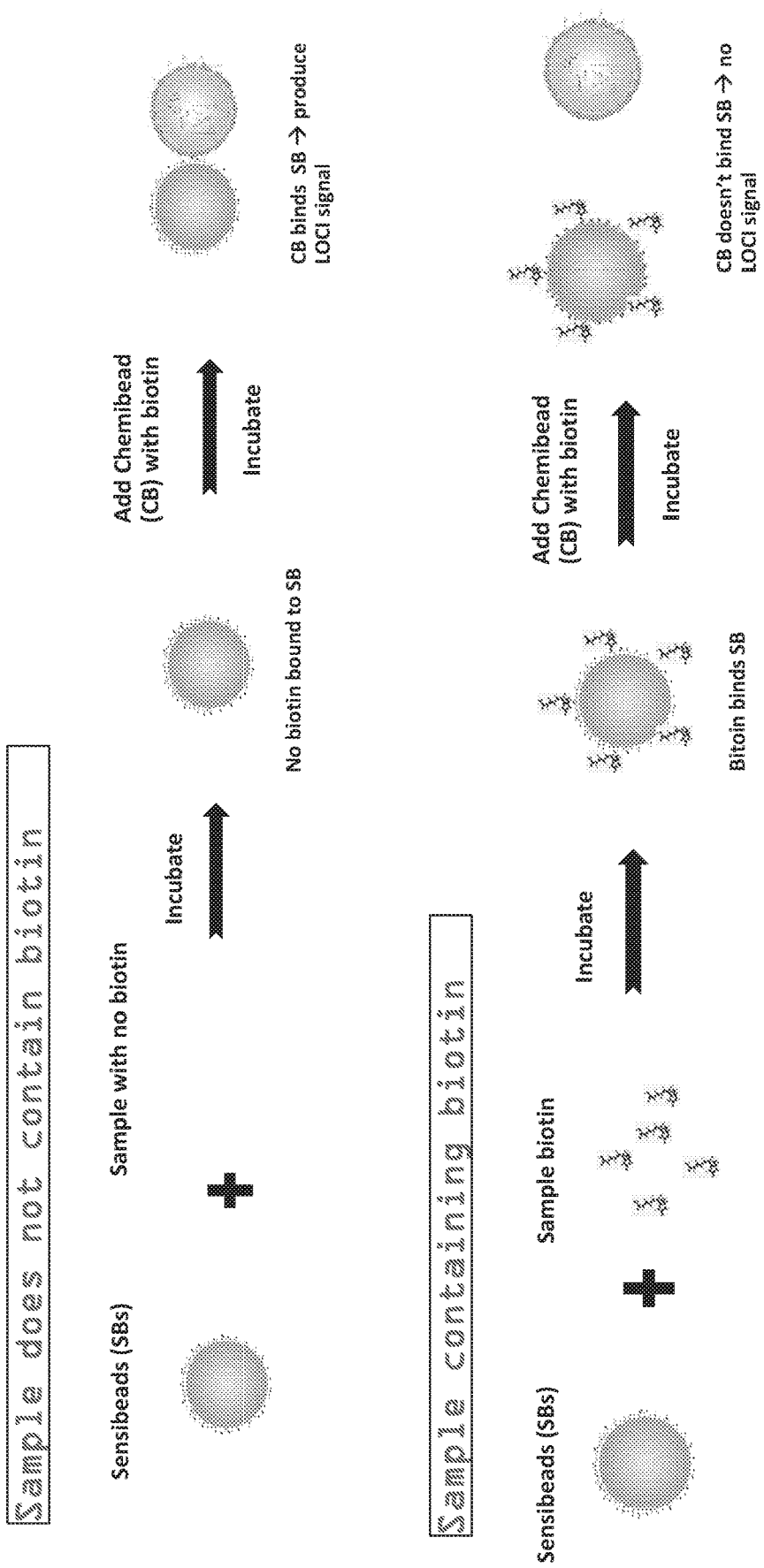
FIG. 1 schematically depicts one non-limiting embodiment of a biotin LOCI® assay constructed in accordance with the present disclosure.

Before explaining at least one embodiment of the present disclosure in detail by way of exemplary language and results, it is to be understood that the present disclosure is not limited in its application to the details of construction and the arrangement of the components set forth in the following description. The present disclosure is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. The foregoing techniques and procedures are generally performed according to conventional methods well known in the art and as described in various general and more specific references that are cited and discussed throughout the present specification. The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses and chemical analyses.

All patents, published patent applications, and non-patent publications mentioned in the specification are indicative of the level of skill of those skilled in the art to which the present disclosure pertains. All patents, published patent applications, and non-patent publications referenced in any portion of this application are herein expressly incorporated by reference in their entirety to the same extent as if each individual patent or publication was specifically and individually indicated to be incorporated by reference.

All of the articles, compositions, kits, and/or methods disclosed herein can be made and executed without undue experimentation in light of the present disclosure. While the articles, compositions, kits, and/or methods have been described in terms of particular embodiments, it will be apparent to those of skill in the art that variations may be applied to the articles, compositions, kits, and/or methods and in the steps or in the sequence of steps of the methods described herein without departing from the concept, spirit, and scope of the present disclosure. All such similar substitutes and modifications apparent to those skilled in the art are deemed to be within the spirit, scope, and concept of the present disclosure as defined by the appended claims.

As utilized in accordance with the present disclosure, the following terms, unless otherwise indicated, shall be understood to have the following meanings:

The use of the term "a" or "an" when used in conjunction with the term "comprising" in the claims and/or the specification may mean "one," but it is also consistent with the meaning of "one or more," "at least one," and "one or more than one." As such, the terms "a," "an," and "the" include plural referents unless the context clearly indicates otherwise. Thus, for example, reference to "a compound" may refer to one or more compounds, two or more compounds, three or more compounds, four or more compounds, or greater numbers of compounds. The term "plurality" refers to "two or more."

The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y, and Z" will be understood to include X alone, Y alone, and Z alone, as well as any combination of X, Y, and Z. The use of ordinal number terminology (i.e., "first," "second," "third," "fourth," etc.) is solely for the purpose of differentiating between two or more items and is not meant to imply any sequence or order or importance to one item over another or any order of addition, for example.

The use of the term "or" in the claims is used to mean an inclusive "and/or" unless explicitly indicated to refer to alternatives only or unless the alternatives are mutually exclusive. For example, a condition "A or B" is satisfied by any of the following: A is true (or present) and B is false (or not present), A is false (or not present) and B is true (or present), and both A and B are true (or present).

As used herein, any reference to "one embodiment," "an embodiment," "some embodiments," "one example," "for example," or "an example" means that a particular element, feature, structure, or characteristic described in connection with the embodiment is included in at least one embodiment. The appearance of the phrase "in some embodiments" or "one example" in various places in the specification is not necessarily all referring to the same embodiment, for example. Further, all references to one or more embodiments or examples are to be construed as non-limiting to the claims.

Throughout this application, the term "about" is used to indicate that a value includes the inherent variation of error for a composition/apparatus/device, the method being employed to determine the value, or the variation that exists among the study subjects. For example, but not by way of limitation, when the term "about" is utilized, the designated value may vary by plus or minus twenty percent, or fifteen percent, or twelve percent, or eleven percent, or ten percent, or nine percent, or eight percent, or seven percent, or six percent, or five percent, or four percent, or three percent, or two percent, or one percent from the specified value, as such variations are appropriate to perform the disclosed methods and as understood by persons having ordinary skill in the art.

As used in this specification and claim(s), the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, when associated with a particular event or circumstance, the term "substantially" means that the subsequently described event or circumstance occurs at least 80% of the time, or at least 85% of the time, or at least 90% of the time, or at least 95% of the time. The term "substantially adjacent" may mean that two items are 100% adjacent to one another, or that the two items are within close proximity to one another but not 100% adjacent to one another, or that a portion of one of the two items is not 100% adjacent to the other item but is within close proximity to the other item.

As used herein, the phrases "associated with" and "coupled to" include both direct association/binding of two moieties to one another as well as indirect association/binding of two moieties to one another. Non-limiting examples of associations/couplings include covalent binding of one moiety to another moiety either by a direct bond or through a spacer group, non-covalent binding of one moiety to another moiety either directly or by means of specific binding pair members bound to the moieties, incorporation of one moiety into another moiety such as by dissolving one moiety in another moiety or by synthesis, and coating one moiety on another moiety, for example.

The terms "analog" and "derivative" are used herein interchangeably and refer to a substance which comprises the same basic carbon skeleton and carbon functionality in its structure as a given compound, but can also contain one or more substitutions thereto. The term "substitution" as used herein will be understood to refer to the replacement of at least one substituent on a compound with a residue R. In certain non-limiting embodiments, R may include H, hydroxyl, thiol, a halogenid selected from fluoride, chloride bromide or iodite, a C1-C4 compound selected one of the following: linear, branched or cyclic alkyl, optionally substituted, and linear branched or cyclic alkenyl, wherein the optional substitutents are selected from one or more alkenylalkyl, alkynylalkyl, cycloalkyl, cycloalkenylalkyl, arylalkyl, heteroarylalkyl, heterocyclealkyl, optionally substituted heterocycloalkenylalkyl, arylcycloalkyl, and arylheterocycloalkyl, each of which is optionally substituted wherein the optional substitutents are selected from one or more of alkenylalkyl, alkynylalkyl, cycloalkyl, cyclalkenylalkyl, arylalkyl, alkylaryl, heteroarylalkyl, heterocyclealkyl, optionally substituted heterocycloalkenylalkyl, arylcycloalkyl, and arylheterocyclalkyl, phenyl, cyano, hydroxyl, alkyl, aryl, cycloalkyl, cyano, alkoxy, alkylthio, amino, —NH (alkyl), —NH(cycloalkyl)$_2$, carboxy, and —C(O))-alkyl.

The term "sample" as used herein will be understood to include any type of biological sample that may be utilized in accordance with the present disclosure. Examples of fluidic biological samples that may be utilized include, but are not limited to, whole blood or any portion thereof (i.e., plasma or serum), urine, saliva, sputum, cerebrospinal fluid (CSF), skin, intestinal fluid, intraperitoneal fluid, cystic fluid, sweat, interstitial fluid, extracellular fluid, tears, mucus, bladder wash, semen, fecal, pleural fluid, nasopharyngeal fluid, combinations thereof, and the like.

Certain non-limiting embodiments of the present disclosure are directed to biotin assay compositions as well as kits containing same and methods of use thereof. In some assay embodiments, signal producing system (sps) members comprise a sensitizer such as, for example, a photosensitizer, and a chemiluminescent composition; in these assay embodiments, activation of the sensitizer results in a product that activates the chemiluminescent composition, thereby generating a detectable signal that relates to the amount of bound and/or unbound biotin being detected. An exemplary (but non-limiting) embodiment of an assay platform on which the present disclosure can be based is the Luminescence Oxygen Channeling Assay (LOCI®; Siemens Healthcare Diagnostics Inc., Tarrytown, N.Y.). The LOCI® assay is described, for example, in U.S. Pat. No. 5,340,716 (Ullman et al.), the entire contents of which are expressly incorporated herein by reference.

Certain non-limiting embodiments of the present disclosure are directed to a kit containing a chemiluminescent detection system for determining the concentration of biotin in a sample. The kit includes: (a) a composition comprising a singlet oxygen-activatable chemiluminescent compound having biotin or an analog thereof (such as, but not limited to, 4'-hydroxyazobenzene-2-carboxylic acid (HABA)) directly or indirectly bound thereto; and (b) a composition comprising a sensitizer capable of generating singlet oxygen in its excited state and having avidin or an analog thereof (such as, but not limited to, streptavidin or traptavidin) directly or indirectly bound thereto, wherein the avidin/avidin analog is capable of binding to biotin in the sample or to (a).

A chemiluminescent compound (chemiluminescer) is a compound that is chemically activatable and, as a result of such activation, emits light at a certain wavelength. Examples of chemiluminescers, by way of illustration and not limitation, include: olefins capable of reacting with singlet oxygen or a peroxide to form hydroperoxides or dioxetanes, which can decompose to ketones or carboxylic acid derivatives; stable dioxetanes which can decompose by the action of light; acetylenes which can react with singlet oxygen to form diketones; hydrazones or hydrazides that can form azo compounds or azo carbonyls such as (but not limited to) luminol; and aromatic compounds that can form endoperoxides, for example. As a consequence of the activation reaction, the chemiluminescers directly or indirectly cause the emission of light.

In certain embodiments, the singlet oxygen-activatable chemiluminescent compound may be a substance that undergoes a chemical reaction with singlet oxygen to form a metastabile intermediate species that can decompose with the simultaneous or subsequent emission of light. The composition comprising the chemiluminescent compound may be directly excited by the activated chemiluminescent compound; alternatively, the composition may further comprise at least one fluorescent molecule that is excited by the activated chemiluminescent compound.

A sensitizer is a molecule, usually a compound, that generates a reactive intermediate such as, for example, singlet oxygen, for activation of a chemiluminescent compound. In some embodiments, the sensitizer is a photosensitizer. Other sensitizers that can be chemi-activated (by, e.g., enzymes and metal salts) include, by way of example and not limitation, other substances and compositions that can produce singlet oxygen with or without activation by an external light source. For example, certain compounds have been shown to catalyze the conversion of hydrogen peroxide to singlet oxygen and water. Non-limiting examples of other sensitizer substances and compositions include: oxides of the alkaline earth metals Ca, Sr, and Ba; derivatives of elements of groups 3A, 4A, 5A, and 6A in $d^0$ configuration; oxides of actinides and lanthanides; and oxidizers $ClO^-$, $BrO^-$, $Au^{3+}$, $IO_3^-$, and $IO_4^-$; and in particular, molybdate, peroxomolybdate, tungstate, and peroxotungstate ions, and acetonitrile. The following references, which are hereby expressly incorporated by reference in their entirety, provide further disclosure regarding sensitizer substances and compositions that also fall within the scope of the presently disclosed and claimed inventive concept: Aubry, *J. Am. Chem. Soc.*, 107:5844-5849 (1985); Aubry, *J. Org. Chem.*, 54:726-728 (1989); Böhme and Brauer, *Inorg. Chem.*, 31:3468-3471 (1992); Niu and Foote, *Inorg. Chem.*, 31:3472-3476 (1992); Nardello et al., *Inorg. Chem.*, 34:4950-4957 (1995); Aubry and Bouttemy, *J. Am. Chem. Soc.*, 119:5286-5294 (1997); and Almeida et al., *Anal. Chim. Acta*, 482:99-104 (2003); the entire contents of each of which are hereby expressly incorporated herein by reference.

Also included within the scope of photosensitizers are compounds that are not true sensitizers but which on excitation by heat, light, ionizing radiation, or chemical activation will release a molecule of singlet oxygen. Members of this class of compounds include, for example (but not by way of limitation), the endoperoxides such as 1,4-biscarboxyethyl-1,4-naphthalene endoperoxide; 9,10-diphenylanthracene-9,10-endoperoxide; and 5,6,11,12-tetraphenyl naphthalene 5,12-endoperoxide. Heating or direct absorption of light by these compounds releases singlet oxygen.

A photosensitizer is a sensitizer for activation of a photoactive compound, for example, by generation of singlet oxygen by excitation with light. The photosensitizers are photoactivatable and include, e.g., dyes and aromatic compounds, and are usually compounds comprised of covalently bonded atoms, usually with multiple conjugated double or triple bonds. The compounds should absorb light in the wavelength range of from about 200 nm to about 1,100 nm, such as (but not limited to) a range of from about 300 nm to about 1,000 nm or a range of from about 450 nm to 950 nm, with an extinction coefficient at its absorbance maximum greater than 500 $M^{-1}$ $cm^{-1}$, or greater than 5,000 $M^{-1}$ $cm^{-1}$, or greater than 50,000 $M^{-1}$ $cm^{-1}$, at the excitation wavelength. Photosensitizers should be relatively photostable and may not react efficiently with singlet oxygen. Examples of photosensitizers, by way of illustration and not limitation, include: acetone; benzophenone; 9-thioxanthone; eosin; 9,10-dibromoanthracene; methylene blue; metallo-porphyrins such as (but not limited to) hematoporphyrin; phthalocyanines; chlorophylls; rose bengal; and buckminsterfullerene; as well as derivatives of these compounds.

Thus, certain non-limiting embodiments of the present disclosure are directed to a kit containing a chemiluminescent detection system for determining the concentration of biotin in a sample, wherein the kit includes: (a) a composition comprising a singlet oxygen-activatable chemiluminescent compound having biotin or an analog thereof directly or indirectly bound thereto; and (b) a composition comprising a sensitizer capable of generating singlet oxygen in its excited state and having traptavidin directly or indirectly bound thereto, wherein the traptavidin is capable of binding to biotin in the sample or to (a). In other non-limiting embodiments, the kit includes: (a) a composition comprising a singlet oxygen-activatable chemiluminescent compound a biotin analog directly or indirectly bound thereto; and (b) a composition comprising a sensitizer capable of generating singlet oxygen in its excited state and having avidin or an analog thereof directly or indirectly bound thereto, wherein the avidin or analog thereof is capable of binding to biotin in the sample or to (a). In yet other non-limiting embodiments, the kit includes: (a) a composition comprising a singlet oxygen-activatable chemiluminescent compound having 4'-hydroxyazobenzene-2-carboxylic acid (HABA) directly or indirectly bound thereto; and (b) a composition comprising a sensitizer capable of generating singlet oxygen in its excited state and having traptavidin directly or indirectly bound thereto, wherein the traptavidin is capable of binding to biotin in the sample or to (a).

Particular, non-limiting examples of compositions comprising chemiluminescent compounds and/or compositions comprising sensitizers that may be utilized in accordance with the present disclosure are set forth in U.S. Pat. Nos. 5,340,716; 5,538,834; 5,545,834; 5,578,498; 5,618,732; 5,672,478; 5,709,994; 5,811,311; 5,780,646; 5,929,049; 5,936,070; 6,002,000; 6,143,514; 6,180,354; 6,251,581; 6,340,599; 6,406,913; 6,406,667; 6,489,309; 6,692,975; 6,703,248; 6,797,481; 6,916,667; 6,949,524; 7,022,529; 7,033,775; 7,101,682; 7,179,660; 7,229,842; and 7,709,273; the entire contents of each of which are hereby expressly incorporated herein by reference.

In a particular (but non-limiting) embodiment, the compositions of (a) and (b) are particles, such as (but not limited to) beads, spheres, spheroids, or liposomes, that have the other listed components coupled thereto and/or disposed therein. A particular (but non-limiting) example of particles that may be utilized in accordance with the present disclosure are latex particles, such as (but not limited to) latex beads. Other non-limiting examples of types of particles that may be utilized as the compositions of (a) and (b) are disclosed in the patents listed in the paragraph above.

Any biotin analog known in the art or otherwise contemplated herein may be utilized in accordance with the present disclosure, so long as the biotin analog is: (1) capable of association with the singlet oxygen-activatable chemiluminescent compound; and (2) capable of binding to the avidin or analog thereof associated with the sensitizer and thereby functioning as a competitor for any biotin present in a sample. Examples of biotin analogs that may be utilized in accordance with the present disclosure include, but are not limited to, those disclosed in Athappilly et al. (*Protein Science* (1997) 6:1338-1342), Torreggiani et al. (*Biospectroscopy* (1998) 4:197-208), Levert et al. (*J Biol Chem* (2002) 277:16347-16350), Yamamoto et al. (*Chem Asian J*, (2015) 10:1071-8), the entire contents of each of which are expressly incorporated herein by reference. Particular non-limiting examples of biotin analogs include 4'-hydroxyazobenzene-2-carboxylic acid (HABA), iminobiotin (such as, but not limited to, 2-imino-biotin (IMBio)), biotin carbonate, biotin carbamate, biotin methyl ester (MEBio), desthiobiotin (DEBio) (such as, but not limited to, d-Desthiobiotin, dl-Desthiobiotin, dl-Desthiobiotin methyl ester, and dl-Desthiobiotinol), diaminobiotin (DABio), chloroacetylated biotin, biotin sulfone, thiobiotin (such as, but not limited to, 2-thiobiotin), methoxycarbonylbiotin methyl ester (1'-N-Methoxycarbonylbiotin methyl ester and 3'-N-Methoxycarbonylbiotin methyl ester), bis-biotin (such as, but not limited to, bis-biotin phosphate ester), tetra-biotin, esters, salts, and/or derivatives of any of the above, and the like. In a particular (but non-limiting) example, the biotin analog is HABA or iminobiotin.

Any avidin analogs known in the art or otherwise contemplated herein may be utilized in accordance with the present disclosure, so long as the avidin or avidin analog is: (1) capable of association with the sensitizer; and (2) capable of binding to any biotin present in a sample; and (3) also capable of binding to the biotin or analog thereof associated with the singlet oxygen-activatable chemiluminescent compound. Non-limiting examples of avidin analogs that can be utilized in accordance with the present disclosure include those disclosed in Kang et al. (*J Drug Target* (1995) 3:159-65), the entire contents of which are expressly incorporated herein by reference. Particular non-limiting examples of avidin analogs include avidin, streptavidin, traptavidin, neutral avidin, Neutralite avidin, Neutravidin, Lite-avidin, succinylated avidin, other forms of modified or genetically engineered) avidin, esters, salts, and/or derivatives of any of the above, and the like.

The reagents of the compositions/kits/methods may be provided in any form that allows them to function in accordance with the present disclosure. For example but not by way of limitation, each of the reagents may be provided in liquid form and disposed in bulk and/or single aliquot form within the kit. Alternatively, in a particular (but non-limiting) embodiment, one or more of the reagents may be disposed in the kit in the form of single aliquot lyophilized reagents. The use of dried reagents in microfluidics devices is described in detail in U.S. Pat. No. 9,244,085 (Samproni), the entire contents of which are hereby expressly incorporated herein by reference.

In addition to the reagents described in detail herein above, the kits may further contain other reagent(s) for conducting any of the particular assays described or otherwise contemplated herein. The nature of these additional reagent(s) will depend upon the particular assay format, and identification thereof is well within the skill of one of ordinary skill in the art; therefore, no further description thereof is deemed necessary. Also, the components/reagents present in the kits may each be in separate containers/ compartments, or various components/reagents can be combined in one or more containers/compartments, depending on the cross-reactivity and stability of the components/ reagents. In addition, the kit may include a microfluidics device in which the components/reagents are disposed.

The relative amounts of the various components/reagents in the kits can vary widely to provide for concentrations of the components/reagents that substantially optimize the reactions that need to occur during the assay methods and further to optimize substantially the sensitivity of an assay. Under appropriate circumstances, one or more of the components/reagents in the kit can be provided as a dry powder, such as a lyophilized powder, and the kit may further include excipient(s) for dissolution of the dried reagents; in this manner, a reagent solution having the appropriate concentrations for performing a method or assay in accordance with the present disclosure can be obtained from these components. Positive and/or negative controls may also be included with the kit. In addition, the kit can further include a set of written instructions explaining how to use the kit. A kit of this nature can be used in any of the methods described or otherwise contemplated herein.

Certain additional non-limiting embodiments of the present disclosure are directed to a microfluidics device that includes the components of any of the kits described herein above. In particular, certain non-limiting embodiments include a microfluidics device for determining the concentration of biotin in a sample, wherein the microfluidics device includes: (a) an inlet channel through which a sample is applied; (b) at least a first compartment capable of being in fluidic communication with the inlet channel, the first compartment containing a sensitizer capable of generating singlet oxygen in its excited state and having any avidin or an analog thereof directly or indirectly bound thereto; and (c) at least a second compartment capable of being in fluidic communication with the first compartment, the second compartment containing a composition comprising a singlet oxygen-activatable chemiluminescent compound having biotin or an analog thereof directly or indirectly bound thereto.

Any of the sensitizers, avidin or analogs thereof, singlet oxygen-activatable chemiluminescent compounds, and biotin or analogs thereof described in detail herein above or otherwise contemplated herein may be utilized in the microfluidics devices of the present disclosure.

In certain particular (but non-limiting) embodiments, the sensitizer of (b) has an avidin analog directly or indirectly bound thereto. Particular non-limiting examples of avidin analogs that can be used include avidin, streptavidin, traptavidin, neutral avidin, Neutralite avidin, Neutravidin, Liteavidin, succinylated avidin, and other forms of modified or genetically engineered avidin, as well as any ester, salt, or derivative of any of the above analogs.

In certain particular (but non-limiting) embodiments, the singlet oxygen-activatable chemiluminescent compound of (c) has a biotin analog directly or indirectly bound thereto. Non-limiting examples of biotin analogs that can be used include 4'-hydroxyazobenzene-2-carboxylic acid (HABA), iminobiotin, biotin carbonate, biotin carbamate, biotin methyl ester, desthiobiotin, diaminobiotin, chloroacetylated biotin, biotin sulfone, thiobiotin, methoxycarbonylbiotin methyl ester, bis-biotin, and tetra-biotin, as well as any ester, salt, or derivative of any of the above analogs. A particular non-limiting example of a biotin analog that can be used is 4'-hydroxyazobenzene-2-carboxylic acid (HABA).

In one non-limiting embodiment, the sensitizer of (b) has traptavidin directly or indirectly bound thereto, and/or the singlet oxygen-activatable chemiluminescent compound of (c) has HABA directly or indirectly bound thereto.

The device may be provided with any arrangement of the compartments and distribution of the two components therebetween that allows the device to function in accordance with the present disclosure.

Any of the compartments of the microfluidics device may be sealed to maintain reagent(s) disposed therein in a substantially air tight environment until use thereof; for example, compartments containing lyophilized reagent(s) may be sealed to prevent any unintentional reconstitution of the reagent. The inlet channel and a compartment, as well as two compartments, may be described as being "capable of being in fluidic communication" with one another; this phrase indicates that each of the compartment(s) may still be sealed, but that the two compartments are capable of having fluid flow therebetween upon puncture of a seal formed therein or therebetween.

The microfluidics devices of the present disclosure may be provided with any other desired features known in the art or otherwise contemplated herein. For example but not by way of limitation, the microfluidics devices of the present disclosure may further include a read chamber; the read chamber may be any of the compartments containing the reagents described herein above, or the read chamber may be in fluidic communication with said compartment. The microfluidics device may further include one or more additional compartments containing other solutions, such as (but not limited to) wash solutions, dilution solutions, excipients, interference solutions, positive controls, negative controls, quality controls, and the like. These additional compartment(s) may be in fluidic communication with one or more of the other compartments. For example, the microfluidics device may further include one or more compartments containing a wash solution, and these compartment(s) may be capable of being in fluidic communication with any other compartment(s) of the device. In another example, the microfluidics device may further include one or more compartments containing an excipient for dissolution of one or more dried reagents, and the compartment(s) may be capable of being in fluidic communication with any other compartment(s) of the device. In yet a further example, the microfluidics device may include one or more compartments containing a dilution solution, and the compartment(s) may be capable of being in fluidic communication with any other compartment(s) of the device.

In addition, any of the kits/microfluidics devices described or otherwise contemplated herein may include multiple assays multiplexed in a single kit/device. When multiple assays are present, each of the assays may be constructed and function as described herein. Alternatively, an assay as described herein may be multiplexed with any other assay known in the art that is capable of being contained within the kits/microfluidics devices of the present disclosure. Non-limiting examples of other assays that may be multiplexed with the assays disclosed and claimed herein include BNP, NT-proBNP, D-Dimer, CKMB, Myoglobin, Myeloperoxidase, ST2, PCT, hCG, LH, FSH, iPTH, TSH, fT$_4$, T4, PSA, fPSA, and cPSA, and combinations thereof.

When multiple assays are present in a single microfluidics device, multiple inlet channels may be connected to the sample application chamber. In certain embodiments, a portion of the sample may be passed from the sample application chamber to the multiple inlet channels without regard for the content thereof. Alternatively, structure(s)

may be present in the sample application chamber, the inlet channels, and/or the connection therebetween that allow for separation of certain components from the whole sample and delivery of said components to the different assays. A non-limiting example of a sample distribution device that may be utilized in accordance with the present disclosure is described in detail in U.S. Pat. No. 9,416,776 (Ledden, et al.), the entire contents of which are hereby expressly incorporated herein by reference.

Certain non-limiting embodiments are also directed to a method for detecting the presence and/or concentration of biotin in a sample. The method includes the steps of: (a) combining, either simultaneously or wholly or partially sequentially: (1) a sample suspected of containing biotin; (2) a composition comprising a singlet oxygen-activatable chemiluminescent compound having biotin or a biotin analog directly or indirectly bound thereto; and (3) an excess of a composition comprising a sensitizer capable of generating singlet oxygen in its excited state and having avidin or an avidin analog directly or indirectly bound thereto; (b) allowing the binding of (3) to biotin present in the sample or to (2), whereby in the absence of biotin, a complex is formed between (2) and (3) and the sensitizer is brought into close proximity to the chemiluminescent compound; (c) activating the sensitizer to generate singlet oxygen, wherein activation of the sensitizer present in the complex causes the activation of the chemiluminescent compound present in the complex; (d) determining the amount of chemiluminescence generated by the activated chemiluminescent compound; (e) optionally repeating steps (b)-(d); and (f) detecting the presence and/or concentration of biotin by analyzing the amount of chemiluminescence so produced, wherein the amount of chemiluminescence is inversely proportional to the amount of biotin in the sample.

Any sample for which an assay for the presence of biotin is desired can be utilized as the sample in accordance with the methods of the present disclosure. Non-limiting examples of samples include a biological sample such as, but not limited to, whole blood or any portion thereof (i.e., plasma or serum), urine, saliva, sputum, cerebrospinal fluid (CSF), skin, intestinal fluid, intraperitoneal fluid, cystic fluid, sweat, interstitial fluid, extracellular fluid, tears, mucus, bladder wash, semen, fecal, pleural fluid, nasopharyngeal fluid, and combinations thereof. Particular non-limiting examples include lysed whole blood cells and lysed red blood cells.

Any of the sensitizers, avidin or analogs thereof, singlet oxygen-activatable chemiluminescent compounds, and biotin or analogs thereof described in detail herein above or otherwise contemplated herein may be utilized in the microfluidics devices of the present disclosure.

In certain particular (but non-limiting) embodiments, the singlet oxygen-activatable chemiluminescent compound of step (a)(2) has a biotin analog directly or indirectly bound thereto. Non-limiting examples of biotin analogs that can be used include 4'-hydroxyazobenzene-2-carboxylic acid (HABA), iminobiotin, biotin carbonate, biotin carbamate, biotin methyl ester, desthiobiotin, diaminobiotin, chloroacetylated biotin, biotin sulfone, thiobiotin, methoxycarbonylbiotin methyl ester, bis-biotin, and tetra-biotin, as well as any ester, salt, or derivative of any of the above analogs. A particular non-limiting example of a biotin analog that can be used is 4'-hydroxyazobenzene-2-carboxylic acid (HABA).

In certain particular (but non-limiting) embodiments, the sensitizer of step (a)(3) has an avidin analog directly or indirectly bound thereto. Particular non-limiting examples of avidin analogs that can be used include avidin, streptavidin, traptavidin, neutral avidin, Neutralite avidin, Neutravidin, Lite-avidin, succinylated avidin, and other forms of modified or genetically engineered avidin, as well as any ester, salt, or derivative of any of the above analogs.

In one non-limiting embodiment, the singlet oxygen-activatable chemiluminescent compound of step (a)(2) has HABA directly or indirectly bound thereto, and/or the sensitizer of step (a)(3) has traptavidin directly or indirectly bound thereto.

When no biotin is present in the sample, a complex of sensitizer and chemiluminescent compound is formed, and a signal is produced. In contrast, if biotin is present in the sample, it binds to the avidin/avidin analog bound to the sensitizer and prevents formation of the complex, thereby preventing production of a signal. Thus, the amount of biotin present in the sample is inversely proportional to the amount of signal produced.

As mentioned above, the various components of the method are provided in combination (either simultaneously or sequentially). When the various components of the method are added sequentially, the order of addition of the components may be varied; a person having ordinary skill in the art can determine the particular desired order of addition of the different components to the assay. The simplest order of addition, of course, is to add all the materials simultaneously and determine the signal produced therefrom. Alternatively, each of the components, or groups of components, can be combined sequentially. In certain embodiments, an incubation step may be involved subsequent to each addition as discussed above.

In an alternative (but non-limiting) embodiment, step (a) of the method includes first combining the sample with the composition comprising the sensitizer having avidin/avidin analog bound thereto and incubating same before adding the composition comprising the singlet oxygen-activatable chemiluminescent compound having biotin/biotin analog bound thereto.

In any non-limiting embodiments of the kits, microfluidics devices, or methods described or otherwise contemplated herein the sensitizer can be a photosensitizer. As such, activation of the photosensitizer will include irradiation with light.

In any non-limiting embodiments of the kits, microfluidics devices, or methods described or otherwise contemplated herein, the singlet oxygen-activatable chemiluminescent compound can be a substance that undergoes a chemical reaction with singlet oxygen to form a metastabile intermediate species that can decompose with the simultaneous or subsequent emission of light.

In addition, in any non-limiting embodiments of the kits, microfluidics devices, or methods described or otherwise contemplated herein, the composition comprising the chemiluminescent compound can further comprise at least one fluorescent molecule that is excited by the activated chemiluminescent compound. In this instance, the methods described or otherwise contemplated herein can further include the step of measuring the amount of light emitted by the fluorescent molecules to determine the amount of analyte in the sample.

EXAMPLES

Examples are provided hereinbelow. However, the present disclosure is to be understood to not be limited in its application to the specific experimentation, results, and laboratory procedures disclosed herein. Rather, the Examples are simply provided as one of various embodiments and are meant to be exemplary, not exhaustive.

Example 1

The present disclosure is directed to a robust biotin LOCI® assay with a wide assay range. The sample size used in certain non-limiting embodiments of this Example is about 20 µl; however, a biotin assay with more extended assay range (e.g., up to 1,500 ng/ml or even 40,000 ng/ml) can be achieved by using a smaller sample size (such as, but not limited to, about 3 µl). However, these sample sizes are not to be construed as limiting of the present disclosure; the use of any sample size that is capable of being assayed falls within the scope of the present disclosure. For example (but not by way of limitation), sample sizes may fall within a range of from about 0.1 µl to about 1,000 µl, or a range of from about 0.5 µl to about 100 µl, or a range of from about 1 µl to about 50 µl, or any integer or non-integer percentage value that falls within any of the above ranges.

The biotin LOCI® assay is schematically depicted in FIG. 1 and described in detail herein below.

The biotin LOCI® assay includes: (i) chemibeads (CBs) coated with biotin or a biotin analog (such as, but not limited to, 4'hydroxyazobenzene-2-carboxylic acid (HABA), or any other biotin analog disclosed or otherwise contemplated herein; and (ii) sensibeads (SBs) coated with avidin or an avidin analog (such as, but not limited to, streptavidin, traptavidin, or any other avidin analog disclosed or otherwise contemplated herein). The biotin/biotin analog-coated chemibeads compete with free biotin in patient samples for binding to the avidin/avidin analog-coated sensibeads. The higher the free biotin concentration in the patient, the less binding of chemibeads and sensibeads is observed, which results in an inverse curve. As described in this Example as well as the later Examples, feasibility of this biotin LOCI® assay using biotin/biotin analog-coated chemibeads and avidin/avidin analog-coated sensibeads has been demonstrated.

Based on the above, a biotin assay (using a biotin LOCI® assay as an example) has been developed. The first step of the assay involves incubation of an excess amount of avidin/avidin analog-coated sensibeads (such as, but not limited to, traptavidin-coated sensibeads) with the sample so that any free biotin present in the sample can be "locked-in" by the sensibeads. Then biotin/biotin analog-coated chemibeads (such as, but not limited to, biotin-coated or HABA-coated chemibeads) are added to scavenge the left-over binding sites from the biotin-avidin binding. If no biotin is present in the sample, then the avidin/avidin analog-coated sensibeads bind to the biotin/biotin analog-coated chemibeads, and a signal is produced (upper panel of FIG. 1). If biotin is present in the sample, the sample biotin binds to the avidin/avidin analog-coated sensibeads, and the sensibeads are no longer able to bind to the biotin/biotin analog-coated chemibeads (lower panel of FIG. 1). Thus, the higher the free biotin concentration in the patient sample, the less binding of chemibeads and sensibeads is observed, resulting in an inverse standard curve.

Example 2

In this Example, the biotin LOCI® assay described in Example 1 was performed using chemibeads (CBs) that were coated with biotin and sensibeads (SBs) that were coated with streptavidin. The sample size utilized was 20 µl. Total reaction volume was 218 µl, and time to first result was 16 minutes.

Figure 2:
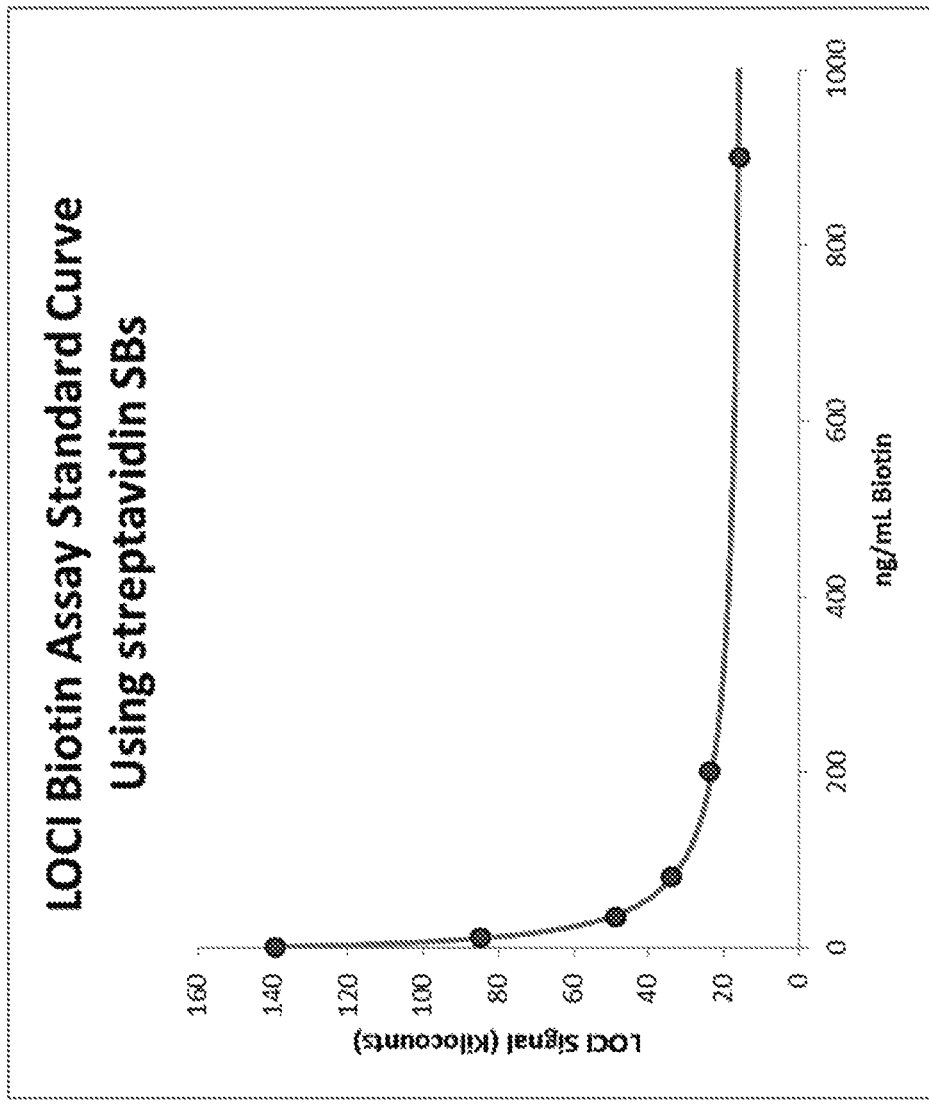
FIG. 2 graphically depicts a standard curve for one non-limiting embodiment of a biotin LOCI® assay constructed in accordance with the present disclosure, wherein the assay that utilizes biotin-coated chemibeads and streptavidin-coated sensibeads.

Data obtained from this biotin LOCI® assay are shown in FIG. 2 and Table 1. As can be seen, a standard curve was obtained over a much wider range of biotin concentrations than any currently available biotin assay.

TABLE 1

| Precision of Biotin LOCl® Assay Using Biotin-CBs and Streptavidin-SBs | | | | | |
|---|---|---|---|---|---|
| Replicate | 0 ng/ml | 10 ng/ml | 35 ng/ml | 80 ng/ml | 200 ng/ml |
| Mean | 0 | 9.9 | 36 | 78 | 186 |
| SD | 0.19 | 0.56 | 1.16 | 2.84 | 7.11 |
| CV | — | 5.7% | 3.2% | 3.7% | 3.9% |

Example 3

In addition to the biotin LOCI® assay embodiments described in Examples 1 and 2, certain additional non-limiting embodiments of the biotin LOCI® assay include the use of biotin analogs and/or avidin analogs. For example (but not by way of limitation), the use of HABA-coated chemibeads and/or traptavidin-coated sensibeads in a biotin LOCI® assay provides multiple advantages over the prior art. First, HABA is a dye that weakly binds with avidin (or streptavidin or traptavidin), and binding of HABA to avidin or an analog thereof is weaker than biotin; as a result, the use of HABA provides a higher sensitivity to the biotin assay because HABA serves as a scavenger (and not a competitor) for biotin binding to sensibeads. Second, due to its unique properties, traptavidin binds to free biotin with one-half the on-rate and ⅒th the off-rate. Therefore, the use of traptavidin provides a "locking" mechanism for free biotin, because once biotin is bound to traptavidin, it hardly dissociates from the binding site.

When traptavidin-coated sensibeads are used, biotin-traptavidin binding "locks" the sample biotin in place with minimal biotin dissociation, and thus the added chemibeads do not compete for traptavidin binding with sample biotin; therefore, the use of traptavidin-coated sensibeads creates a hapten assay with more robust precision. In addition, due to no competition from sample biotin, the assay signal is more linearly proportional to free biotin concentration in a wider dynamic range, resulting in an extended assay range when compared to regular competitive assays.

Thus, in certain non-limiting embodiments, the unique features of traptavidin (alone or in combination with the use of HABA or another biotin analog) are utilized to create a biotin assay with robust precision and an extended dynamic range.

Example 4

Figure 3:
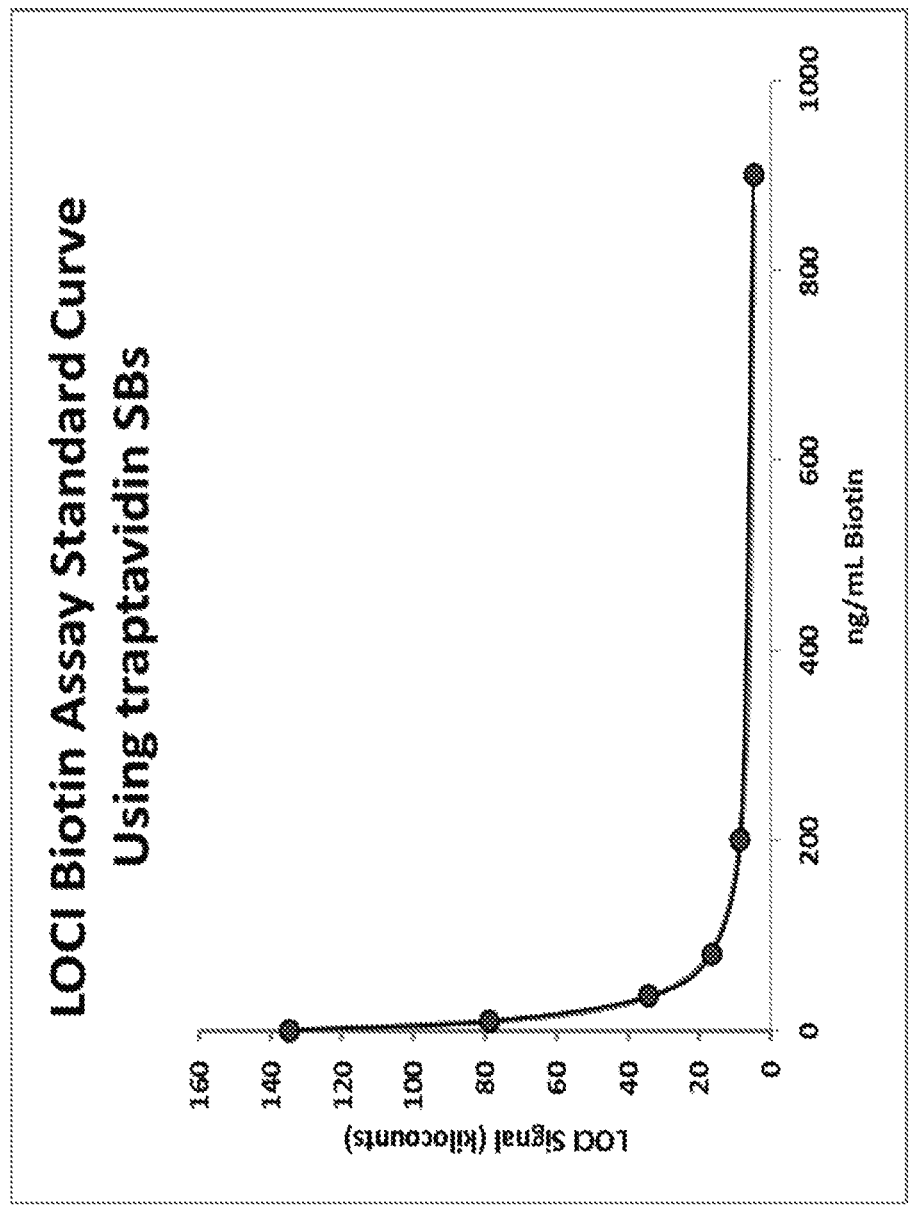
FIG. 3 graphically depicts a standard curve for another non-limiting embodiment of a biotin LOCI® assay constructed in accordance with the present disclosure, wherein the assay utilizes biotin-coated chemibeads and traptavidin-coated sensibeads.

In this Example, the biotin LOCI® assay described in Example 3 was performed using chemibeads (CBs) that were coated with biotin and sensibeads (SBs) that were coated with traptavidin. Data obtained from this biotin LOCI® assay are shown in FIG. 3 and Table 2. As can be seen, a standard curve was obtained over a much wider range of biotin concentrations than any currently available biotin assay.

TABLE 2

Precision of Biotin LOCI® Assay
Using Biotin-CBs and Traptavidin-SBs

| Replicate | 0 ng/ml | 10 ng/ml | 35 ng/ml | 80 ng/ml | 200 ng/ml |
|---|---|---|---|---|---|
| Mean | 0 | 9.4 | 35 | 84 | 205 |
| SD | 0.296 | 0.54 | 0.98 | 2.34 | 5.39 |
| CV | — | 5.7% | 2.8% | 2.8% | 2.6% |

Figure 4:
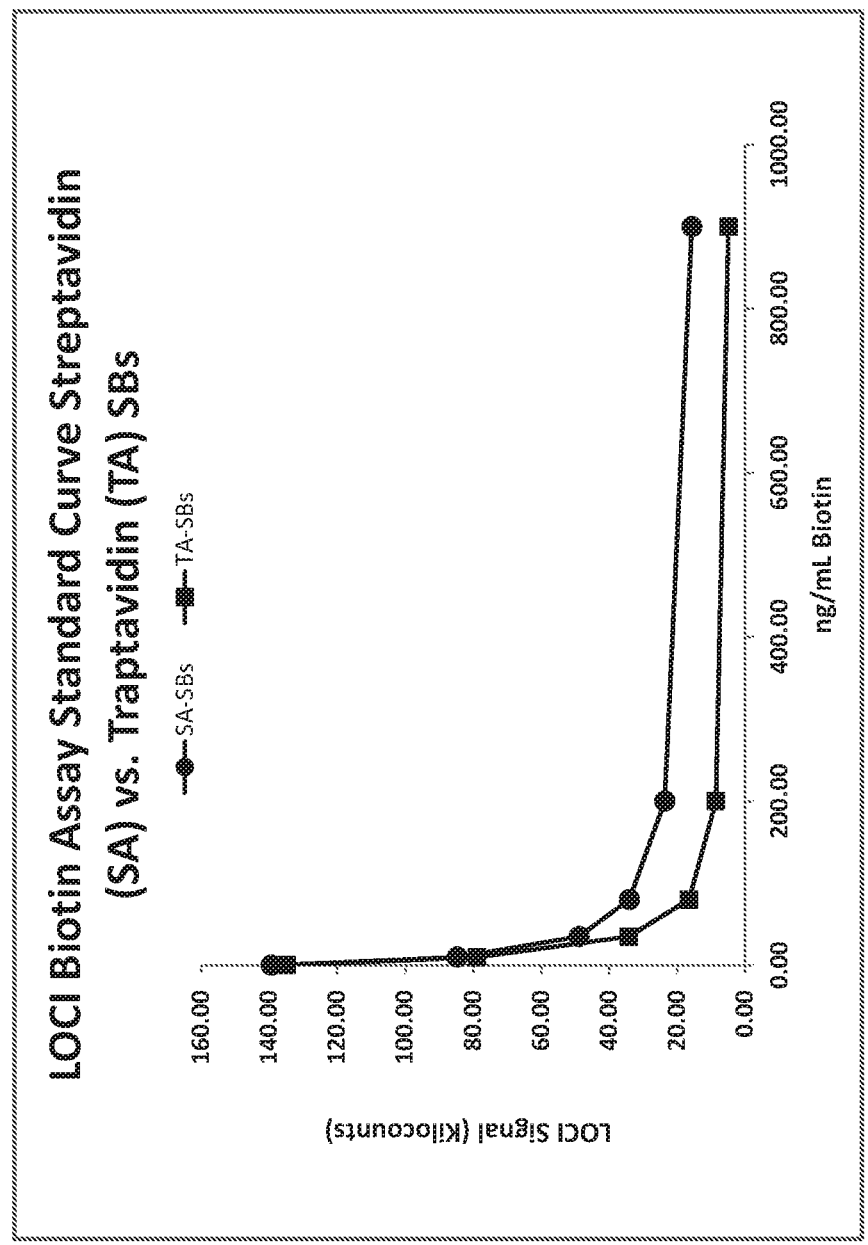
FIG. 4 graphically depicts a comparison of the standard curves from FIGS. 2 and 3.

In general, except for 0 ng/mL, sensibeads coated with traptavidin showed significant precision improvement over the streptavidin-coated sensibeads, due to traptavidin's ten-times slower off rate that locks (or "traps") the bound sample biotin in place on the sensibead surface (see FIG. 4 and Tables 1 and 2). In addition, the traptavidin-SB curve is steeper than that of the streptavidin-SB (FIG. 4).

Example 5

Figure 5:
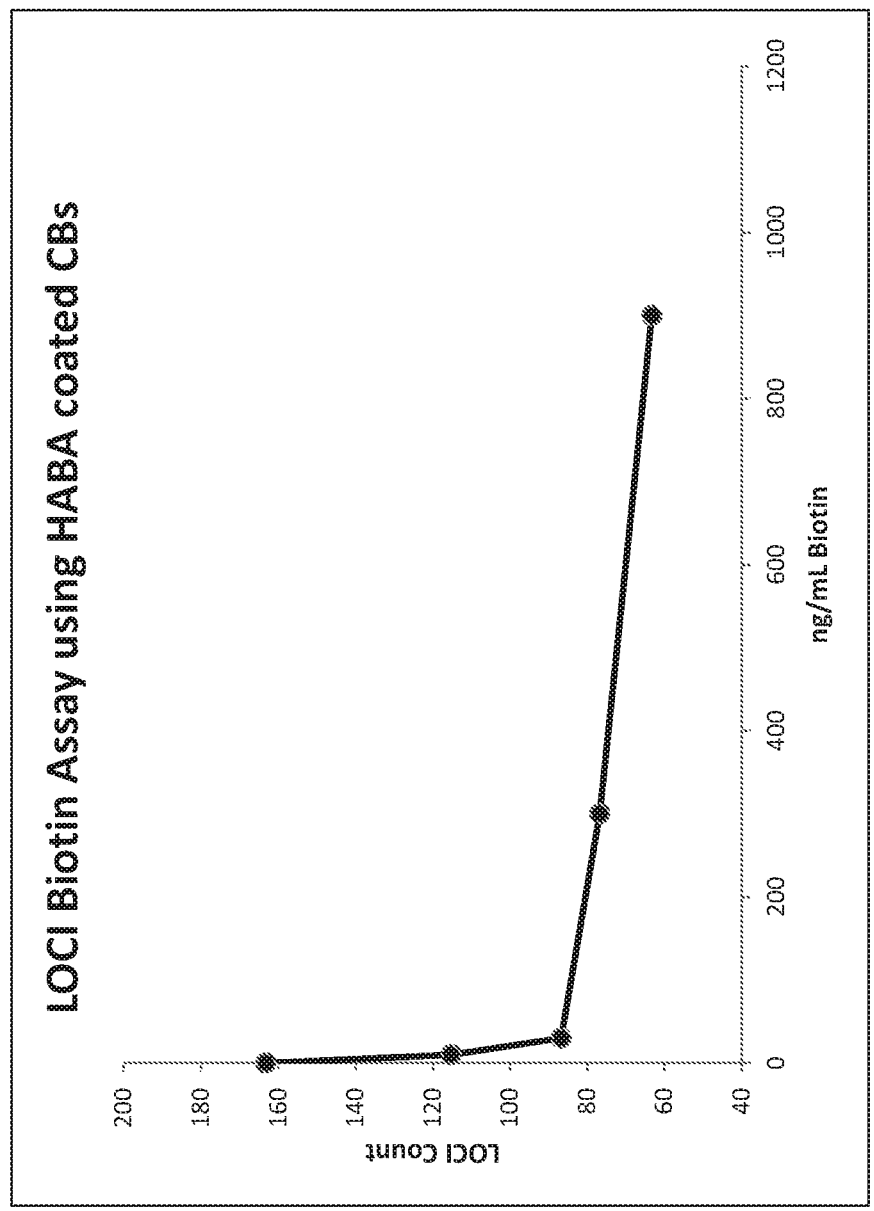
FIG. 5 graphically depicts a standard curve for yet another non-limiting embodiment of a biotin LOCI® assay constructed in accordance with the present disclosure, wherein the assay utilizes 4'-hydroxyazobenzene-2-carboxylic acid (HABA)-coated chemibeads and streptavidin-coated sensibeads.

In this Example, the biotin LOCI® assay described in Example 3 was performed using chemibeads (CBs) that were coated with HABA and sensibeads (SBs) that were coated with streptavidin. Data obtained from this biotin LOCI® assay are shown in FIG. 5. As can be seen, a standard curve was obtained over a much wider range of biotin concentrations than any currently available biotin assay.

Example 6

Figure 6:
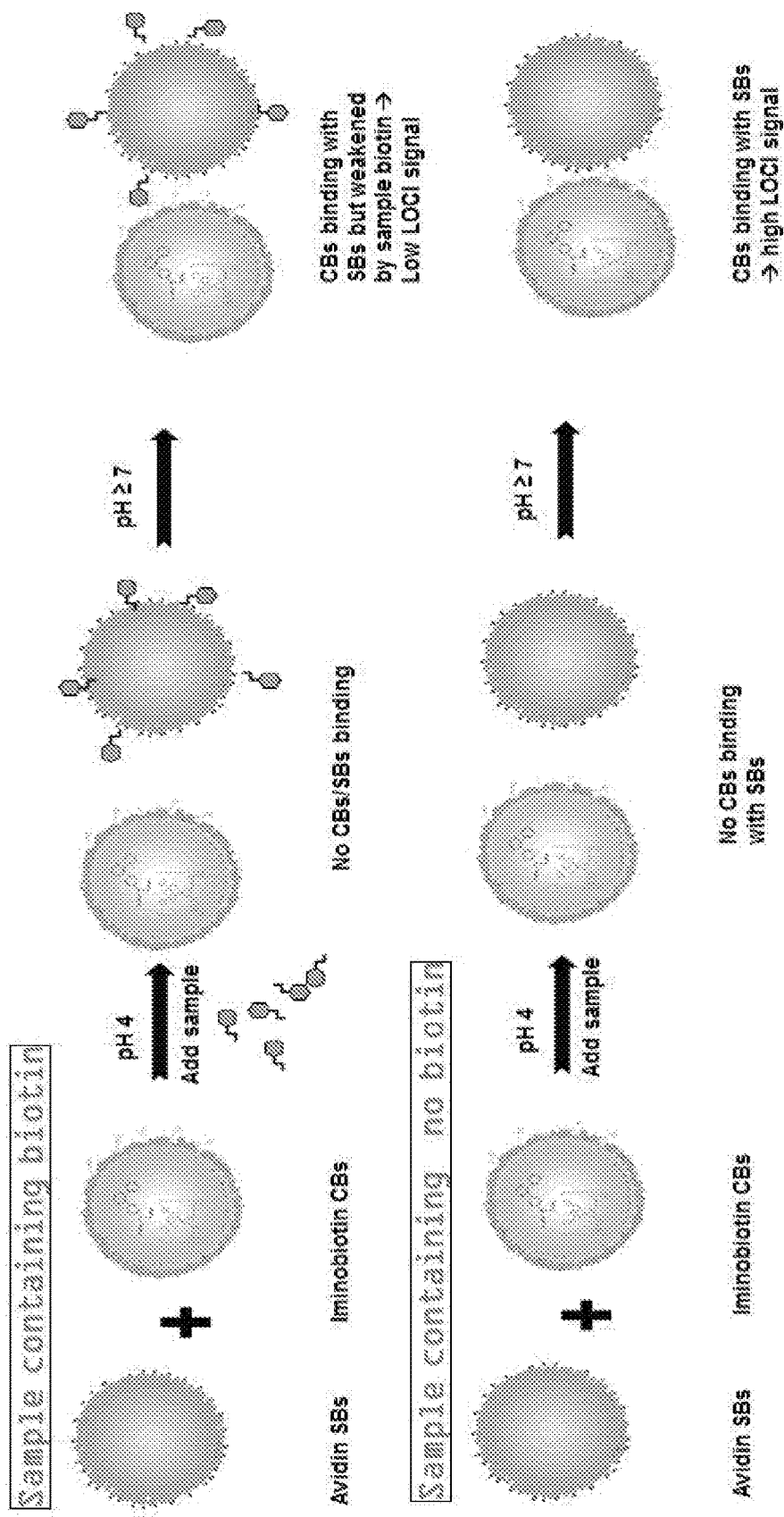
FIG. 6 schematically depicts yet another non-limiting embodiment of a biotin LOCI® assay constructed in accordance with the present disclosure, wherein the assay utilizes iminobiotin-coated chemibeads and avidin-coated sensibeads.

FIG. 6 depicts another non-limiting embodiment of a biotin LOCI® assay in which iminobiotin-coated chemibeads are utilized. In this Example, chemibeads are coated with imino-biotin, and sensibeads are coated with either streptavidin or traptavidin. Iminobiotin has a pH dependent binding to avidin; iminobiotin has higher affinity with avidin at a higher pH and dissociates from avidin when the pH is low. Using this feature, the iminobiotin-coated CBs can be incubated with SBs and samples at a lower pH to ensure biotin binding to SBs. After the binding of SBs and biotin is complete, the pH is increased to enable CBs and SBs binding, hence generating LOCI signal.

Thus, in accordance with the present disclosure, there have been provided compositions, kits, and devices, as well as methods of producing and using same, which fully satisfy the objectives and advantages set forth hereinabove. Although the present disclosure has been described in conjunction with the specific drawings, experimentation, results, and language set forth hereinabove, it is evident that many alternatives, modifications, and variations will be apparent to those skilled in the art. Accordingly, it is intended to embrace all such alternatives, modifications, and variations that fall within the spirit and broad scope of the present disclosure.

What is claimed is:

1. A kit containing a chemiluminescent detection system for determining the concentration of biotin in a sample, the kit comprising:
    (a) a composition comprising a particle having a singlet oxygen-activatable chemiluminescent compound coupled thereto and/or disposed therein, the particle having biotin or an analog thereof directly or indirectly bound thereto, wherein the singlet oxygen-activatable chemiluminescent compound is a substance that undergoes a chemical reaction with singlet oxygen to form a metastabile intermediate species that can decompose with the simultaneous or subsequent emission of light; and
    (b) a composition comprising a particle having a sensitizer capable of generating singlet oxygen in its excited state coupled thereto and/or disposed therein, the particle having traptavidin directly or indirectly bound thereto; and
    wherein the kit is capable of detecting biotin concentrations in a range of from about 0 to about 1500 ng/ml;
    wherein the biotin analog is selected from the group consisting of 4'-hydroxyazobenzene-2-carboxylic acid (HABA), iminobiotin, biotin carbonate, biotin carbamate, biotin methyl ester, desthiobiotin, diaminobiotin, chloroacetylated biotin, biotin sulfone, thiobiotin, methoxycarbonylbiotin methyl ester, bis-biotin, tetrabiotin, and an ester or salt of any of the above biotin analogs.

2. The kit of claim 1, wherein the biotin analog is HABA or iminobiotin.

3. The kit of claim 1, wherein the composition comprising the chemiluminescent compound further comprises at least one fluorescent molecule that is excited by the activated chemiluminescent compound.

4. The kit of claim 1, wherein the sensitizer is a photosensitizer.

5. A kit containing a chemiluminescent detection system for determining the concentration of biotin in a sample, the kit comprising:
    (a) a composition comprising a particle having a singlet oxygen-activatable chemiluminescent compound coupled thereto and/or disposed therein, the particle having 4'-hydroxyazobenzene-2-carboxylic acid (HABA) directly or indirectly bound thereto; and
    (b) a composition comprising a particle having a sensitizer capable of generating singlet oxygen in its excited state coupled thereto and/or disposed therein, the particle having traptavidin directly or indirectly bound thereto;
    wherein the kit is capable of detecting biotin concentrations in a range of from about 0 to about 1500 ng/ml;
    wherein the singlet oxygen-activatable chemiluminescent compound is a substance that undergoes a chemical reaction with singlet oxygen to form a metastabile intermediate species that can decompose with the simultaneous or subsequent emission of light.

6. A method for detecting the presence and/or concentration of biotin in a sample, the method comprising the steps of:
    (a) combining, either simultaneously or wholly or partially sequentially:
        (1) a sample suspected of containing biotin;
        (2) a composition comprising a particle having a singlet oxygen-activatable chemiluminescent compound coupled thereto and/or disposed therein, the particle having biotin or a biotin analog directly or indirectly bound thereto, wherein the singlet oxygen-activatable chemiluminescent compound is a substance that undergoes a chemical reaction with singlet oxygen to form a metastabile intermediate species that can decompose with the simultaneous or subsequent emission of light; and
        (3) an excess of a composition comprising a particle having a sensitizer capable of generating singlet oxygen in its excited state coupled thereto and/or disposed therein, the particle having traptavidin directly or indirectly bound thereto;

(b) allowing the binding of (3) to biotin present in the sample or to (2), whereby in the absence of biotin, a complex is formed between (2) and (3) and the sensitizer is brought into close proximity to the chemiluminescent compound;

(c) activating the sensitizer to generate singlet oxygen, wherein activation of the sensitizer present in the complex causes the activation of the chemiluminescent compound present in the complex;

(d) determining the amount of chemiluminescence generated by the activated chemiluminescent compound;

(e) optionally repeating steps (b)-(d); and (f) detecting the presence and/or concentration of biotin by analyzing the amount of chemiluminescence so produced, wherein the amount of chemiluminescence is inversely proportional to the amount of biotin in the sample; and wherein the method is capable of detecting biotin concentrations in a range of from about 0 to about 1500 ng/ml;

wherein the biotin analog is selected from the group consisting of 4'-hydroxyazobenzene-2-carboxylic acid (HABA), iminobiotin, biotin carbonate, biotin carbamate, biotin methyl ester, desthiobiotin, diaminobiotin, chloroacetylated biotin, biotin sulfone, thiobiotin, methoxycarbonylbiotin methyl ester, bis-biotin, tetra-biotin, and an ester or salt of any of the above biotin analogs.

7. The method of claim 6, wherein the particle of step (a)(2) has HABA directly or indirectly bound thereto.

8. The method of claim 6, wherein the sensitizer is a photosensitizer, and the activation of the sensitizer in step (c) comprises irradiation with light.

9. The method of claim 6, wherein the sample is a biological sample.

10. The method of claim 9, wherein the biological sample is selected from the group consisting of whole blood or any portion thereof, urine, saliva, sputum, cerebrospinal fluid, skin, intestinal fluid, intraperitoneal fluid, cystic fluid, sweat, interstitial fluid, extracellular fluid, tears, mucus, bladder wash, semen, fecal, pleural fluid, nasopharyngeal fluid, and combinations thereof.

11. The method of claim 9, wherein the biological sample comprises at least one of lysed whole blood cells and lysed red blood cells.

12. The method of claim 6, wherein the composition comprising the chemiluminescent compound further comprises at least one fluorescent molecule that is excited by the activated chemiluminescent compound.

13. The method of claim 12, further comprising the step of measuring the amount of light emitted by the fluorescent molecules to determine the amount of analyte in the sample.

* * * * *